(12) United States Patent
Thurlkill

(10) Patent No.: US 7,581,717 B1
(45) Date of Patent: Sep. 1, 2009

(54) FAN BLADE SCENT DISPERSING SYSTEM

(76) Inventor: Clifford K. Thurlkill, 2523 44th St. S., Saint Petersburg, FL (US) 33711

( * ) Notice: Subject to any disclaimer, the term of this patent is extended or adjusted under 35 U.S.C. 154(b) by 600 days.

(21) Appl. No.: 11/388,137

(22) Filed: Mar. 24, 2006

(51) Int. Cl.
*B01D 47/00* (2006.01)

(52) U.S. Cl. .................. 261/30; 261/DIG. 88; 239/56; 239/57; 422/124

(58) Field of Classification Search .................. 261/30, 261/104, DIG. 88; 239/55, 56, 57; 422/124
See application file for complete search history.

(56) References Cited

U.S. PATENT DOCUMENTS

| | | | |
|---|---|---|---|
| D334,800 S | 4/1993 | Portis | |
| 5,383,765 A | 1/1995 | Baxter et al. | |
| 5,460,787 A * | 10/1995 | Colon | 422/123 |
| 5,775,876 A | 7/1998 | Walker et al. | |
| 5,935,526 A | 8/1999 | Moore | |
| 6,241,219 B1 | 6/2001 | Logan et al. | |
| 2003/0012680 A1 | 1/2003 | Balsys | |
| 2003/0190268 A1 | 10/2003 | Saverd | |

* cited by examiner

*Primary Examiner*—Robert A Hopkins

(57) ABSTRACT

A fan blade scent dispersing system includes a ceiling fan that includes a plurality of fan blades. Each of the fan blades has a blade portion and an arm portion. Each of the blade portions has an upper surface and a lower surface. A housing has a top wall, a bottom wall and a peripheral wall that is attached to and extends between the top and bottom walls. Each of the top, bottom and peripheral walls has an outer surface and an inner surface with respect to an interior of the housing. The housing has a plurality of slots therein extending into the outer surface and through the inner surface. A scent impregnated panel is positioned within the housing. The panel is configured for releasing scent impregnated therein. A coupling member is attached to the housing and releasably secures the housing to one of the arm portions.

7 Claims, 4 Drawing Sheets

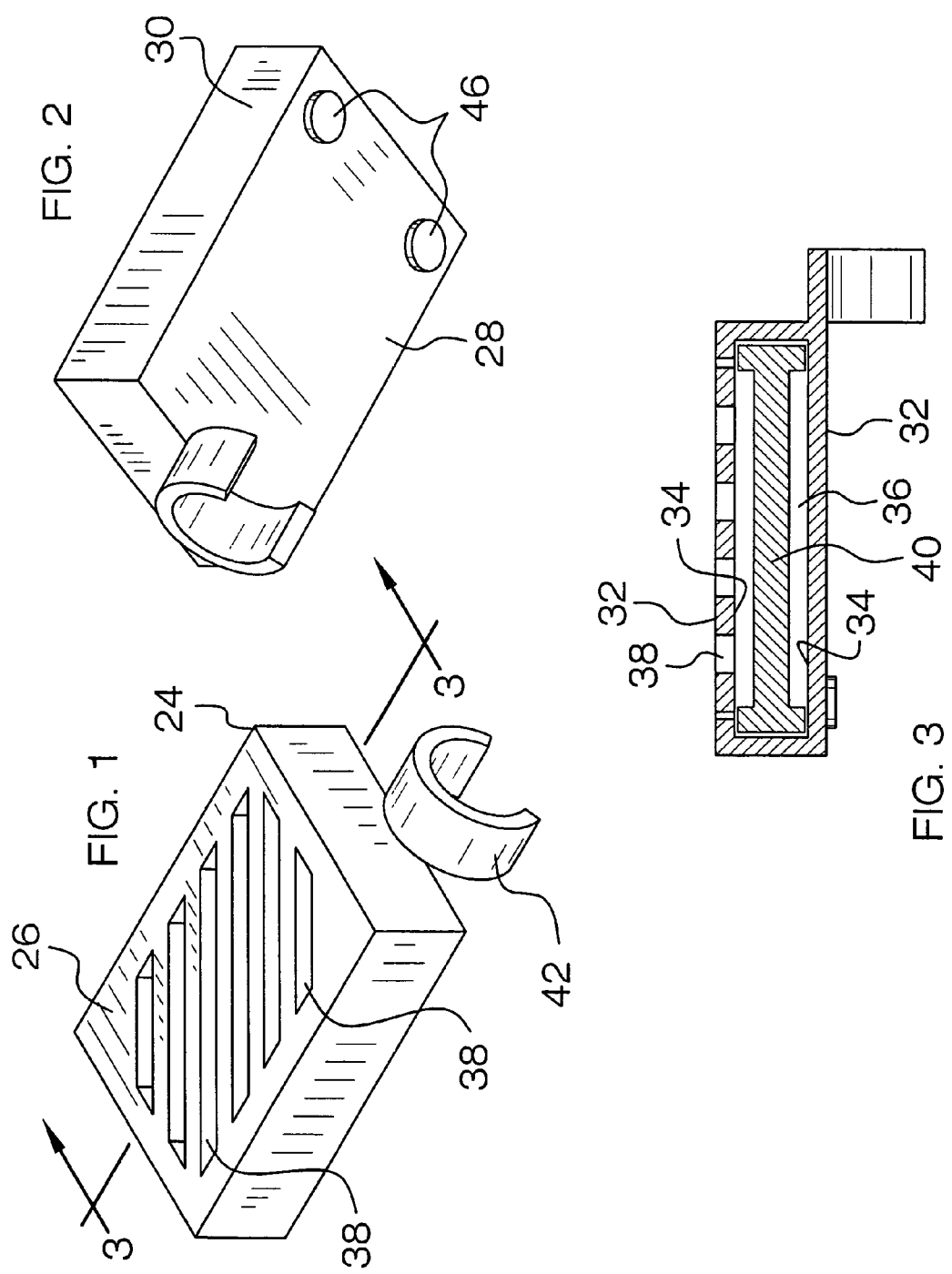

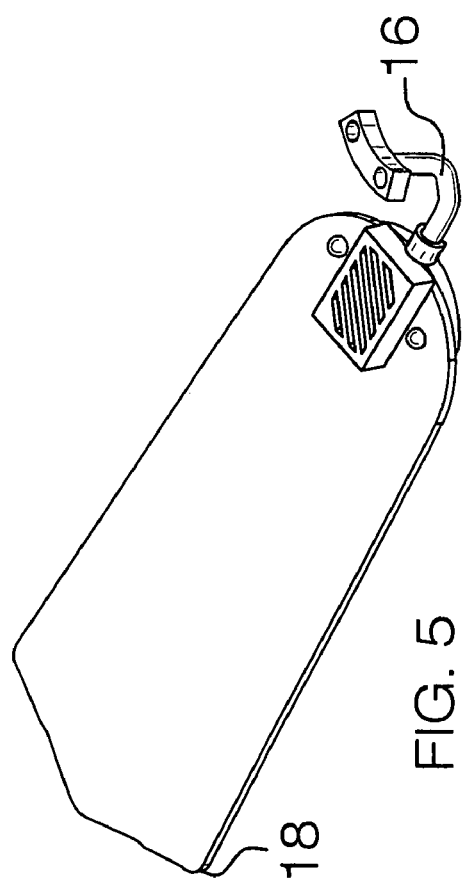
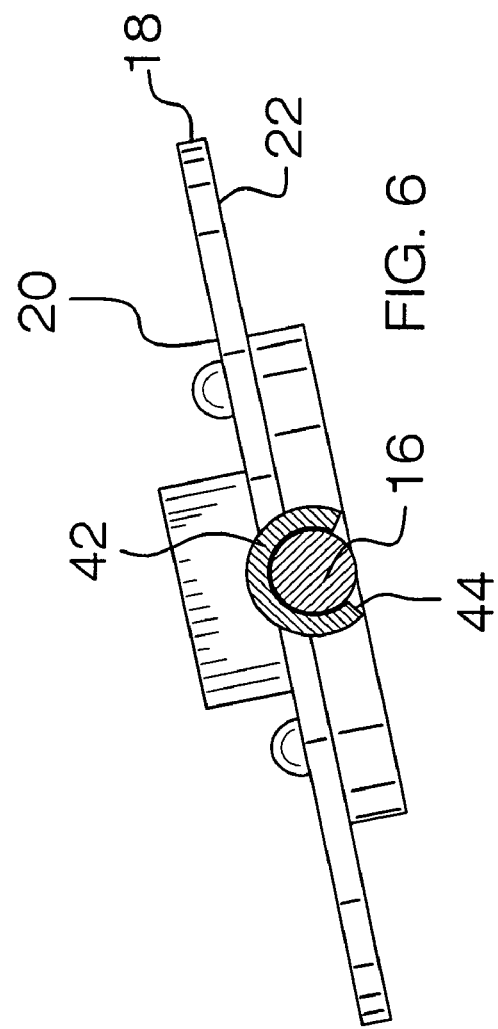

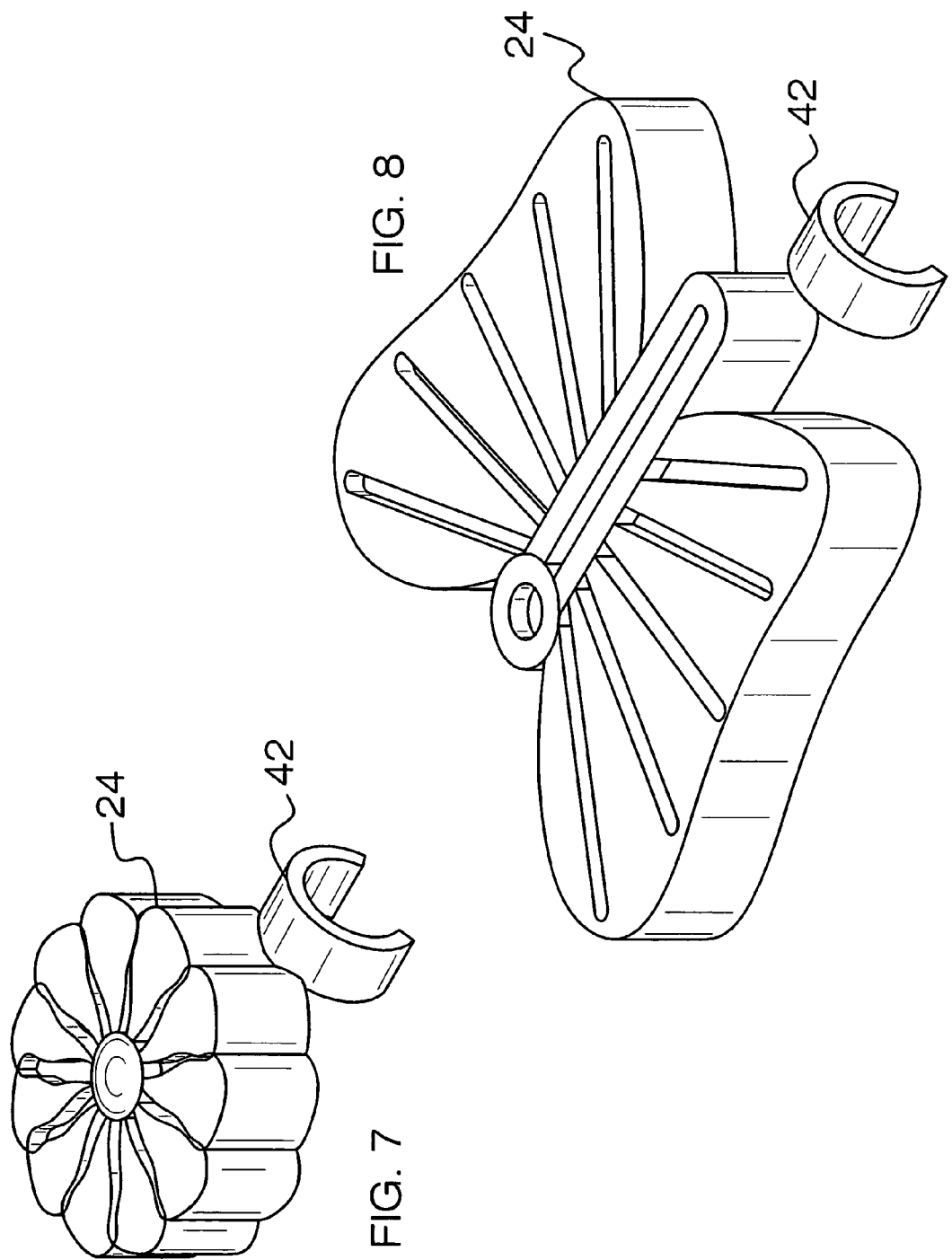

FAN BLADE SCENT DISPERSING SYSTEM

BACKGROUND OF THE INVENTION

1. Field of the Invention

The present invention relates to scent dispersing devices and more particularly pertains to a new scent dispersing device that is attachable to and dispenses a fragrance from a ceiling fan.

2. Description of the Prior Art

The use of scent dispersing devices is known in the prior art. While these devices fulfill their respective, particular objectives and requirements, the need remains for a dispersing system that utilizes the rotational motion of a ceiling fan. In particular, the system should include a means for attaching a scent dispersing device to a fan blade so that the scent dispersing device is not viewed and is securely attached to the fan blade.

SUMMARY OF THE INVENTION

The present invention meets the needs presented above by generally comprising a ceiling fan that includes a plurality of fan blades. Each of the fan blades has a blade portion and an arm portion. Each of the blade portions has an upper surface and a lower surface. A housing has a top wall, a bottom wall and a peripheral wall that is attached to and extends between the top and bottom walls. Each of the top, bottom and peripheral walls has an outer surface and an inner surface with respect to an interior of the housing. The housing has a plurality of slots therein extending into the outer surface and through the inner surface. A scent impregnated panel is positioned within the housing. The panel is configured for releasing scent impregnated therein. A coupling member is attached to the housing and releasably secures the housing to one of the arm portions.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a top perspective view of a housing of a fan blade scent dispersing system according to the present invention.

FIG. 2 is a bottom perspective view of the housing of the present invention.

FIG. 3 is a cross-sectional view taken along line 3-3 of FIG. 1 of the present invention.

FIG. 5 is a perspective view of the present invention.

FIG. 6 is a cross-sectional view taken along line 6-6 of FIG. 4 of the present invention.

FIG. 7 is a perspective view of an alternate embodiment of the present invention.

FIG. 8 is a perspective view of a second alternate embodiment of the present invention.

DESCRIPTION OF THE PREFERRED EMBODIMENT

Figure 4:
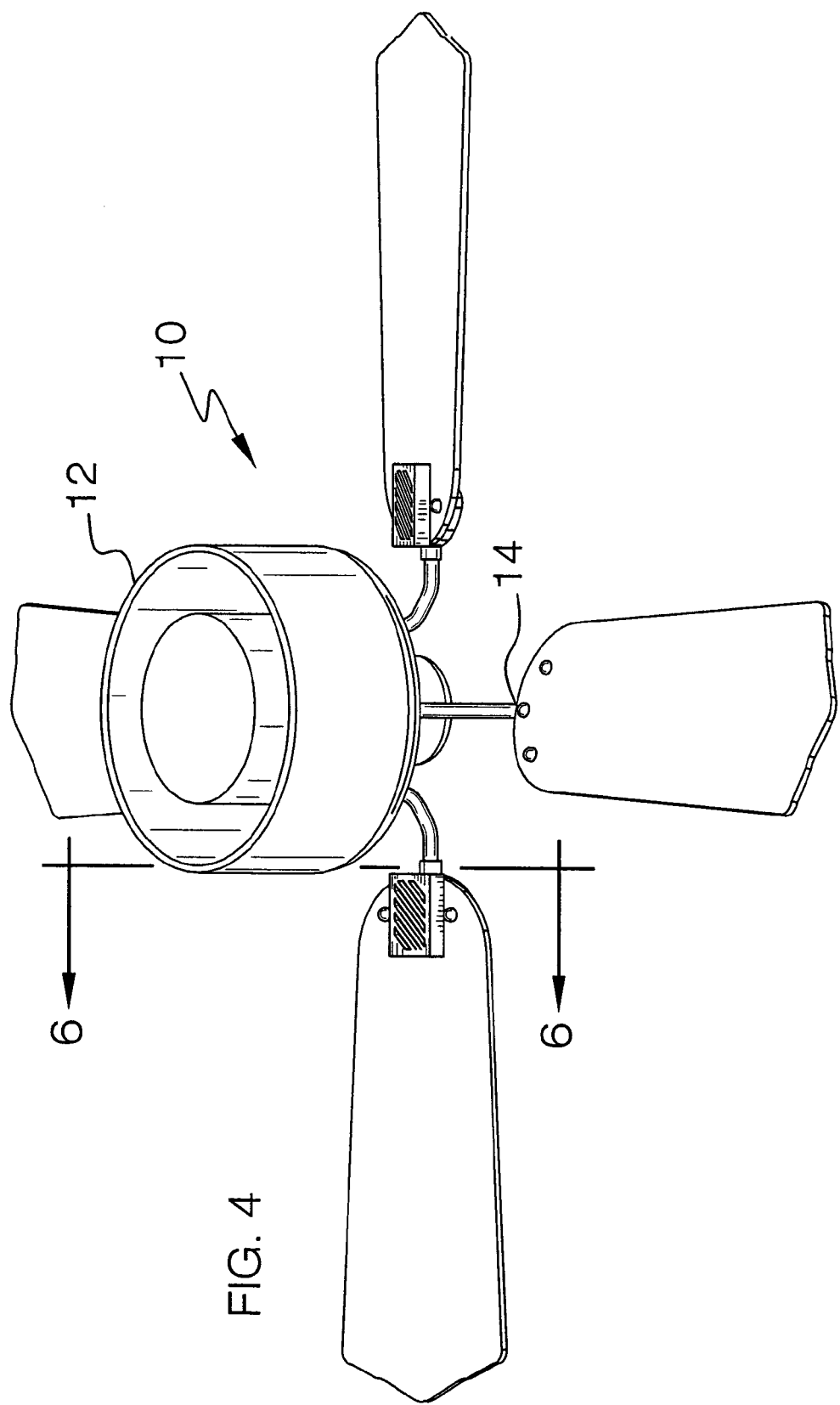
FIG. 4 is a perspective view of the present invention.

With reference now to the drawings, and in particular to FIGS. 1 through 8 thereof, a new scent dispersing device embodying the principles and concepts of the present invention and generally designated by the reference numeral 10 will be described.

As best illustrated in FIGS. 1 through 8, the fan blade scent dispersing system 10 generally comprises a conventional ceiling fan 12 that includes a plurality of fan blades 14. Each of the fan blades 14 includes a blade portion 16 and an arm portion 18. Each of the blade portions 16 has an upper surface 20 and a lower surface 22.

A housing 24 has a top wall 26, a bottom wall 28 and a peripheral wall 30 that is attached to and extends between the top 26 and bottom 28 walls. Each of the top 26, bottom 28 and peripheral 30 walls has an outer surface 32 and an inner surface 34 with respect to an interior 36 of the housing 24. The top wall 26 has a plurality of slots 38 therein extending into the outer surface 32 and through the inner surface 34. A scent impregnated panel 40 is positioned within the housing 24. The panel 40 is configured for releasing scent impregnated therein. The panel 40 may be comprised of any conventional absorbent material used for absorbing and releasing a fragrance.

A coupling member 42 is attached to the housing 24 and releasably secures the housing 24 to one of the arm portions 16. The coupling member 42 comprises a loop having a break 44 therein. The coupling member 42 is positioned on the peripheral wall 30 and adjacent to the bottom wall 28. The break 44 is directed away from the top wall 26 and extends along a line bisecting the housing 24. The housing 24 is positioned on the upper surface 20 of the blade portion 18 when the coupling member 42 is attached to a corresponding one of the arm portions 16. The respective arm portion 16 is extended through the break 44.

A plurality of cushioning pads 46 is attached to an outer surface 32 of the bottom wall 28 to prevent vibration of the housing 24 on the blade portion 18 and to assist in stabilizing the housing 24 on the blade portion 18. At least one of the cushioning pads 46 is positioned opposite of the coupling member 42. Each of the cushioning pads 46 is comprised of a resiliently compressible material.

In use, the housing 24 is attached to one of the arm portions 16 as described above and shown in the Figures. The ceiling fan 12, when turned on, causes air to flow into and out of the slots 38 to increase the rate of scent dispersal. FIGS. 7 and 8 show various housing 24 designs.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A scent dispensing system comprising:
   a ceiling fan including a plurality of fan blades, each of said fan blades including a blade portion and an arm portion, each of said blade portions having an upper surface and a lower surface;
   a housing having a top wall, a bottom wall and a peripheral wall being attached to and extending between said top and bottom walls, each of said top, bottom and peripheral walls having an outer surface and an inner surface with respect to an interior of said housing, said housing having a plurality of slots therein extending into said outer surface and through said inner surface;
   a scent impregnated panel being positioned within said housing, said panel being configured for releasing scent impregnated therein;
   a coupling member being attached to said housing and releasably securing said housing to one of said arm portions, said coupling member comprising a loop having a break therein, said arm portion being extendable through said break, said coupling member being positioned on said peripheral wall and adjacent to said bottom wall, said break being directed away from said top wall, said housing being positioned on said upper surface of said blade portion when said coupling member is attached to a corresponding one of said arm portions.

2. The system according to claim 1, wherein said slots are positioned in said top wall.

3. The system according to claim 1, further including a plurality of cushioning pads being attached to an outer surface of said bottom wall.

4. The system according to claim 3, wherein at least one of said cushioning pads is positioned opposite of said coupling member.

5. The system according to claim 1, further including a plurality of cushioning pads being attached to an outer surface of said bottom wall.

6. The system according to claim 5, wherein at least one of said cushioning pads is positioned opposite of said coupling member.

7. A scent dispensing system comprising:
   a ceiling fan including a plurality of fan blades, each of said fan blades including a blade portion and an arm portion, each of said blade portions having an upper surface and a lower surface,
   a housing having a top wall, a bottom wall and a peripheral wall being attached to and extending between said top and bottom walls, each of said top, bottom and peripheral walls having an outer surface and an inner surface with respect to an interior of said housing, said top wall having a plurality of slots therein extending into said outer surface and through said inner surface;
   a scent impregnated panel being positioned within said housing, said panel being configured for releasing scent impregnated therein;
   a coupling member being attached to said housing and releasably securing said housing to one of said arm portions, said coupling member comprising a loop having a break therein, said coupling member being positioned on said peripheral wall and adjacent to said bottom wall, said break being directed away from said top wall, said housing being positioned on said upper surface of said blade portion when said coupling member is attached to a corresponding one of said arm portions; and
   a plurality of cushioning pads being attached to an outer surface of said bottom wall, at least one of said cushioning pads being positioned opposite of said coupling member, each of said cushioning pads being comprised of a resiliently compressible material.

* * * * *